United States Patent
Williams et al.

(10) Patent No.: US 8,077,943 B2
(45) Date of Patent: Dec. 13, 2011

(54) METHOD AND APPARATUS FOR ALIGNING A MULTI-MODALITY IMAGING SYSTEM

(75) Inventors: John Jay Williams, Hartland, WI (US); Gang Cheng, Elm Grove, WI (US); Xiaoquan Zhao, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 947 days.

(21) Appl. No.: 12/045,246

(22) Filed: Mar. 10, 2008

(65) Prior Publication Data
US 2009/0226066 A1 Sep. 10, 2009

(51) Int. Cl.
*G06K 9/00* (2006.01)
(52) U.S. Cl. .................... 382/128; 378/205
(58) Field of Classification Search .............. 382/128, 382/130–132, 289, 294–297; 378/63, 205, 378/209
See application file for complete search history.

(56) References Cited

U.S. PATENT DOCUMENTS

| | | | |
|---|---|---|---|
| 6,674,834 B1 | 1/2004 | Acharya et al. | 378/18 |
| 6,739,751 B2 | 5/2004 | Williams | 378/205 |
| 7,103,233 B2 | 9/2006 | Stearns | 382/289 |
| 2006/0173270 A1 | 8/2006 | Weiner et al. | 600/407 |

*Primary Examiner* — Courtney Thomas
(74) *Attorney, Agent, or Firm* — Dean D. Small; The Small Patent Law Group

(57) ABSTRACT

A method of determining component misalignment in a multi-modality imaging system includes imaging a plurality of target objects with a first modality unit to generate a tomographic image data set and imaging the plurality of targets with a second modality unit to generate an emission image data set. The method also includes determining a location of the target objects in the emission image data set to produce emission target object location coordinates, calculating a positional alignment vector for each target object based on the emission target object location coordinates, and aligning the multi-modality imaging system based on the positional alignment vectors.

26 Claims, 7 Drawing Sheets

METHOD AND APPARATUS FOR ALIGNING A MULTI-MODALITY IMAGING SYSTEM

BACKGROUND OF THE INVENTION

This invention relates generally to imaging systems capable of operation in multiple modalities, and more particularly to an apparatus and method for aligning a multi-modality imaging system.

Multi-modal imaging systems are capable of scanning using different modalities, such as, for example, but not limited to, Positron Emission Tomography (PET) and Computed Tomography (CT). The difference between multi-mode and multi-modality is that in multi-mode systems the same hardware is utilized to perform scans in different modes (e.g., a radiation source and a radiation detector is used in both a flouro mode and a tomosynthesis mode), while in a multi-modal system (multi-modality system), although some of the same hardware is utilized to perform different scans (e.g., an image produced by PET is processed and displayed respectively, by the same computer and display as an image produced by CT), the data acquisition systems (hereinafter sometimes termed "modality unit") are different. For example, on a CT/PET system a radiation source and a radiation detector are used in tandem to acquire CT data, while a radiopharmaceutical is typically employed in tandem with a PET camera to acquire PET data. It is contemplated that the benefits of the invention accrue to all multi-modality imaging systems, such as, for example, but not limited to, a CT/PET imaging system as well as systems utilizing currently unknown modalities as well as currently unfeasible combinations, such as, for example, but not limited to, a combination PET/ultrasound system and/or a CT/MRI system.

In multi-modality systems, for example, an integrated PET-CT system the PET and CT should be inherently registered with one another. Since the patient lies still on the same table during the PET and CT portions of the acquisition, the patient should be in a consistent position and orientation during the two acquisitions, greatly simplifying the process of correlating and fusing the CT and PET images. The CT image is then used to provide attenuation correction information for the reconstruction of PET images. An image reader correlates the anatomic information presented in the CT image and the functional information presented in the PET image. Inherent registration of the CT and PET images assumes a perfect alignment of the PET and CT detector coordinate systems, or at least a known spatial transformation between the two coordinate systems. However, misalignment of the coordinate systems will directly result in a mis-registration of the images.

One previously proposed method for aligning components of a multi-modality image system is to compare the positions of a known attenuation object using both CT and PET attenuation measurements. For example, to align a CT imaging system fabricated as part of the multimodality imaging system the attenuation object is irradiated with an x-ray beam. An electrical signal that represents the intensity of the impinging x-ray beam and attenuation of the x-ray beam is received at a detector. When the second imaging modality is a PET imaging system the PET imaging system is modified to generate attenuation data. Specifically, additional equipment is installed on the PET system to obtain the attenuation data. While accurate, this process may be time consuming and limited by the statistical uncertainty in the transmission acquisition. As a result, utilizing attenuation data to align both the CT imaging system and the PET imaging system results in increased costs of the overall dual imaging system and an increased time to perform the alignment.

BRIEF DESCRIPTION OF THE INVENTION

In one embodiment a method of determining component misalignment in a multi-modality imaging system is provided. The method includes imaging a plurality of target objects with a first modality unit to generate a transmission image data set and imaging the plurality of target objects with a second modality unit to generate an emission image data set. The method also includes determining a location of the target objects in the emission image data set to produce emission target object location coordinates, calculating a positional alignment vector for each target object based on the emission target object location coordinates, and aligning the multi-modality imaging system based on the positional alignment vectors.

In another embodiment, a multi-modality imaging system is provided. The system includes a first modality unit having a bore therethrough, a second modality unit having a bore therethrough, and a table positioned to move at least partially through the first modality unit bore and the second modality bore. The system also includes a computer operationally coupled to the first and second modality units. The computer is programmed to image a plurality of target objects with the first modality unit to generate a transmission image data set and image the plurality of target objects with the second modality unit to generate an emission image data set. The computer is also programmed to determine a location of the target objects in the emission image data set to produce emission target object location coordinates, and calculate a positional alignment vector for each target object based on the emission target object location coordinates, the positional alignment vectors are then used to align the multi-modality imaging system.

In a further embodiment a computer readable medium is provided. The computer readable medium is programmed to determine a location of the target objects in the transmission image data set and determine a location of the same target objects in the emission image data set. The computer readable medium is also programmed to determine a location of the target objects in the emission image data set to produce emission target object location coordinates, and calculate a positional alignment vector for each target object based on the emission target object location coordinates, the positional alignment vectors are then used to align the multi-modality imaging system.

DETAILED DESCRIPTION OF THE INVENTION

Figure 1:
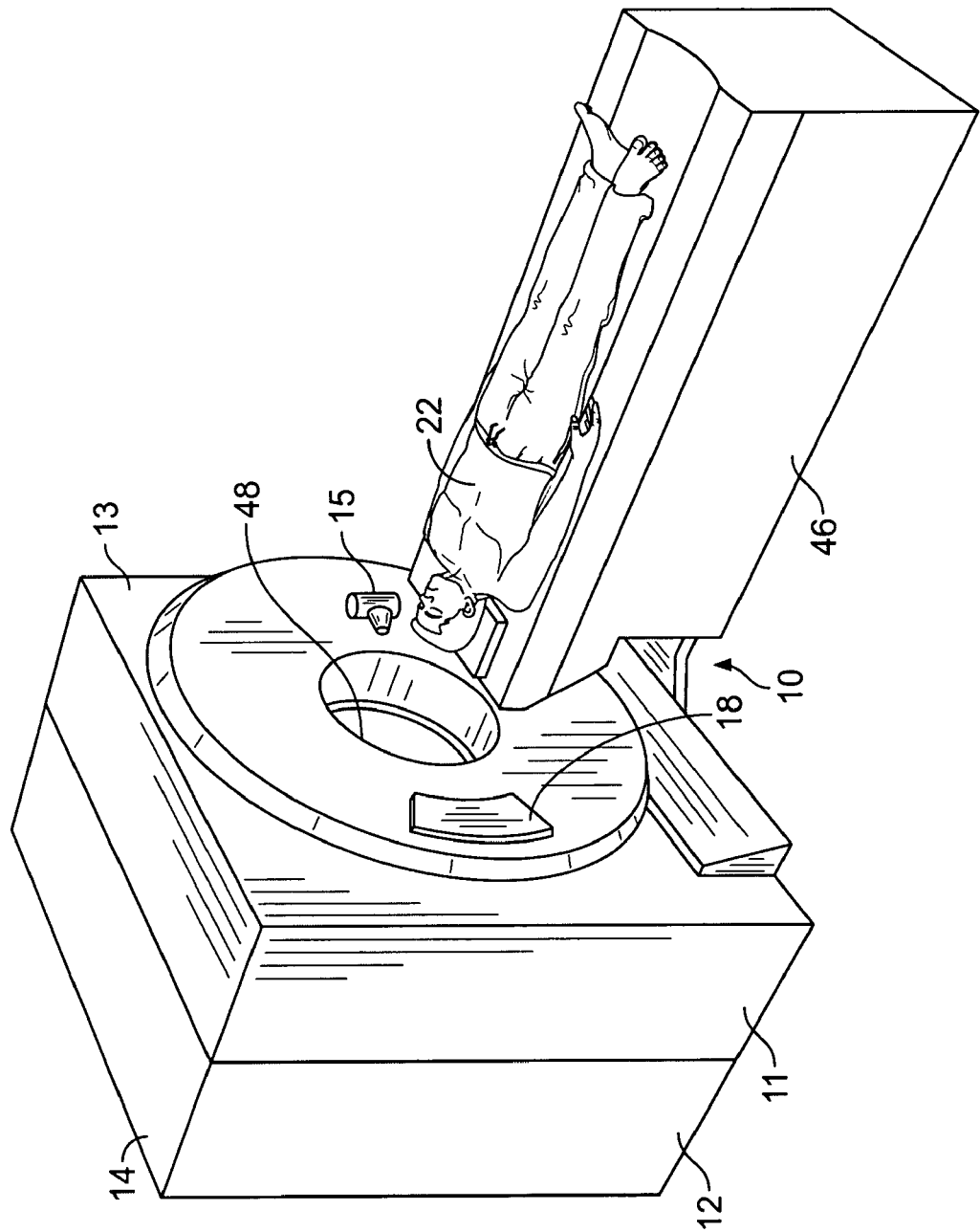
FIG. 1 is a pictorial view of an exemplary multi-modal imaging system in accordance with an embodiment of the present invention.

Although embodiments of the present invention are described in the context of an exemplary dual modality imaging system that includes a CT imaging system and a PET imaging system it should be understood that other imaging systems capable of performing the functions described herein are contemplated as being used.

The CT imaging system includes an x-ray source that projects a fan-shaped beam which is collimated to lie within an X Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In some CT imaging systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

At least some CT systems are configured to also perform Positron Emission Tomography (PET) and are referred to as CT/PET systems. Positrons are positively charged electrons (anti-electrons) which are emitted by radio nuclides that have been prepared using a cyclotron or other device. The radio nuclides most often employed in diagnostic imaging are fluorine-18 (18F), carbon-11 (11C), nitrogen-13 (13N), and oxygen-15 (15O). Radio nuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, vessel or the like, which is to be imaged. It is known that specific radiopharmaceuticals become concentrated within certain organs or, in the case of a vessel, that specific radiopharmaceuticals will not be absorbed by a vessel wall. The process of concentrating often involves processes such as glucose metabolism fatty acid metabolism and protein synthesis. Hereinafter, in the interest of simplifying this explanation, an organ to be imaged including a vessel will be referred to generally as an "organ of interest" and the invention will be described with respect to a hypothetical organ of interest.

After the radiopharmaceutical becomes concentrated within an organ of interest and while the radio nuclides decay the radio nuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using photon emission tomography (PET). First, each gamma ray has an energy of approximately 511 keV upon annihilation. Second, the two gamma rays are directed in substantially opposite directions.

In PET imaging, if the general locations of annihilations can be identified in three dimensions, a three dimensional image of an organ of interest can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known back projection procedures to construct the three dimensional image of the organ of interest.

As used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
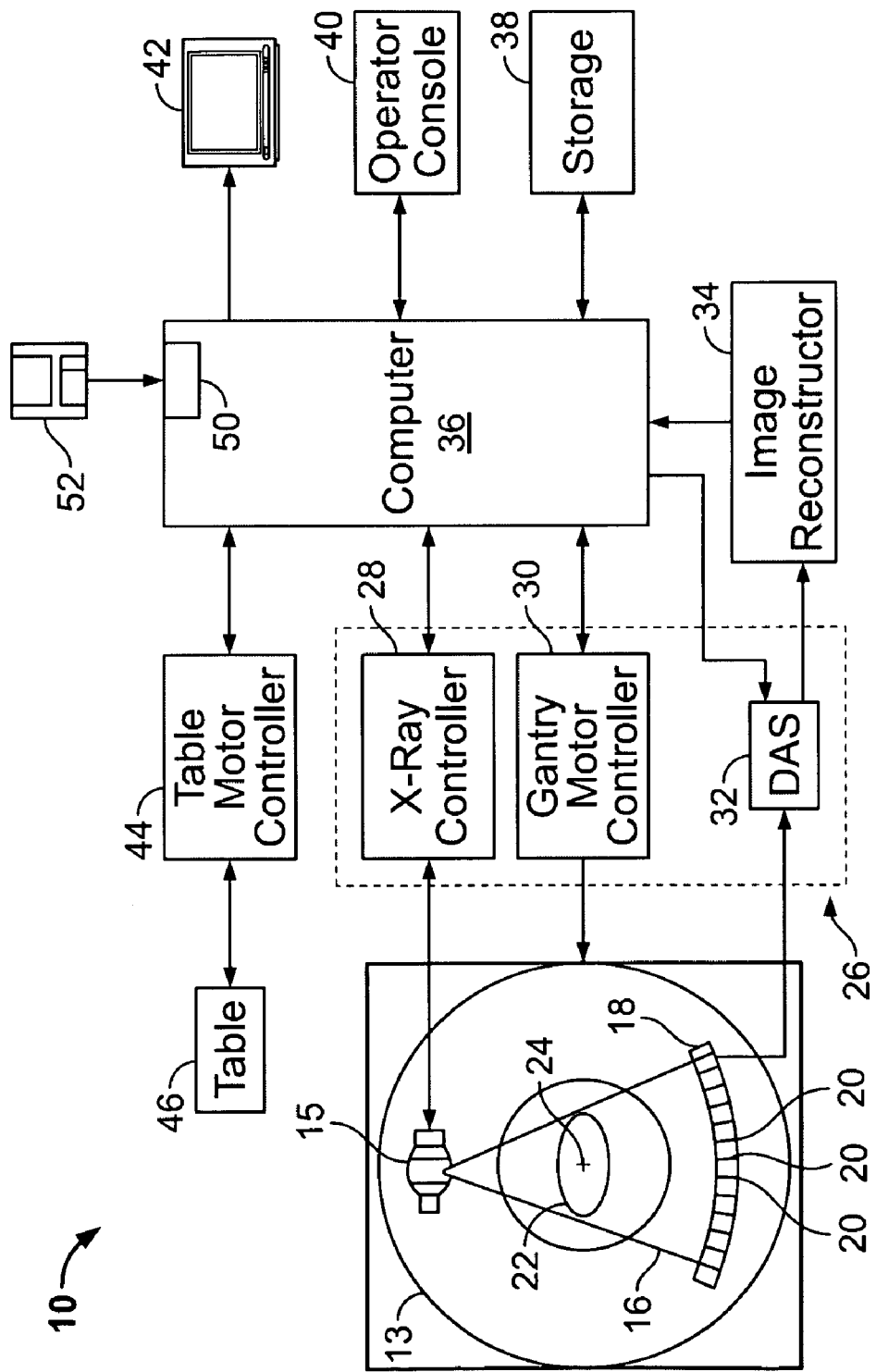
FIG. 2 is a schematic illustration of a Computed Tomography imaging system that may be used with the dual modality imaging system shown in FIG. 1 in accordance with an another embodiment of the present invention.

FIG. 1 is a pictorial view of an exemplary multi-modal imaging system 10 in accordance with an embodiment of the present invention. FIG. 2 is a schematic illustration of a first modality unit 11 that may be used with the dual modality imaging system shown in FIG. 1 in accordance with an embodiment of the present invention. It should be realized that the imaging system illustrated in FIGS. 1 and 2 are exemplary only, and the methods and apparatus described herein may also be used with imaging systems that utilize other geometries, such as ring source, step and shoot, etc.

Referring to FIGS. 1 and 2, the multi-modal imaging system 10 includes the first modality unit 11 and a second modality unit 12. The two modality units enable the multi-modal imaging system 10 to scan an object or patient in a first modality using the first modality unit 11 and to scan the object or patient in a second modality using the second modality unit 12. The multi-modal imaging system 10 allows for multiple scans in different modalities to facilitate an increased diagnostic capability over single modality systems. In one embodiment multi-modal imaging system 10 is a Computed Tomography/Positron Emission Tomography (CT/PET) imaging system 10. The CT/PET system 10 is shown as including a gantry 13 representative of a "third generation" CT imaging system i.e. the first modality 11, and a gantry 14 associated with a PET imaging system i.e. the second modality unit 12. Optionally modalities other than CT and PET may be employed with the multi-modal imaging system 10. For example, the modalities may include an ultrasound imaging system a Magnetic Resonance Imaging (MRI) system or any imaging system that is configured to generate tomographic images.

The gantry 13 includes an x-ray source 15 that projects a beam of x-rays 16 (shown in FIG. 2) toward a detector array 18 on the opposite side of the gantry 13. Detector array 18 is formed by a plurality of detector rows (not shown) including a plurality of detector elements 20 which together sense the projected x-rays that pass through an exemplary alignment object 100 (shown in FIG. 3) or the medical patient 22. Each detector element 20 produces an electrical signal that represents the intensity of an impinging x-ray beam and hence allows estimation of the attenuation of the beam as it passes through the alignment object 100 or patient 22. During a scan to acquire x-ray projection data, gantry 13 and the components mounted thereon rotate about a center of rotation 24.

FIG. 2 shows only a single row of detector elements 20 (i.e., a detector row). However, a multislice detector array 18 includes a plurality of parallel detector rows of detector elements 20 such that projection data corresponding to a plurality of quasi-parallel or parallel slices can be acquired simultaneously during a scan.

Rotation of gantry 13 and the operation of x-ray source 15 are governed by a control mechanism 26 of CT/PET system 10. Control mechanism 26 includes an x-ray controller 28 that provides power and timing signals to x-ray source 15 and a gantry motor controller 30 that controls the rotational speed and position of gantry 13. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position the alignment object 100 or patient 22 in gantry 13. Particularly table 46 moves the alignment object 100 or portions of the patient 22 through gantry opening 48.

In one embodiment computer 36 includes a device 50, for example, a floppy disk drive or CD-ROM drive, for reading instructions and/or data from a computer-readable medium 52, such as a floppy disk or CD-ROM. In another embodiment computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. CT/PET system 10 also includes a plurality of PET cameras including a plurality of detectors. The PET detectors and detector array 18 both detect radiation and are both referred to herein as radiation detectors. In one embodiment CT/PET system 10 is a Discovery LS CT/PET system commercially available from General Electric Medical Systems, Waukesha Wis., and configured as herein described.

Additionally, although described in a medical setting, it is contemplated that the benefits of the invention accrue to all CT systems including industrial CT systems such as, for example, but not limited to, a baggage scanning CT system typically used in a transportation center such as, for example, but not limited to, an airport or a rail station.

Figure 3:
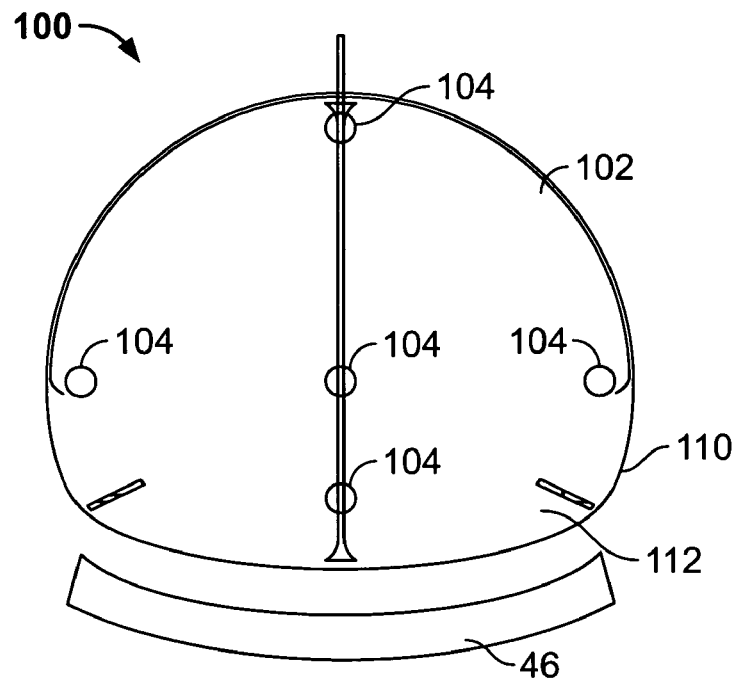
FIG. 3 is an end view of an exemplary alignment object that may be used with the dual modality imaging system shown in FIG. 1 in accordance with an embodiment of the present invention.
Figure 4:
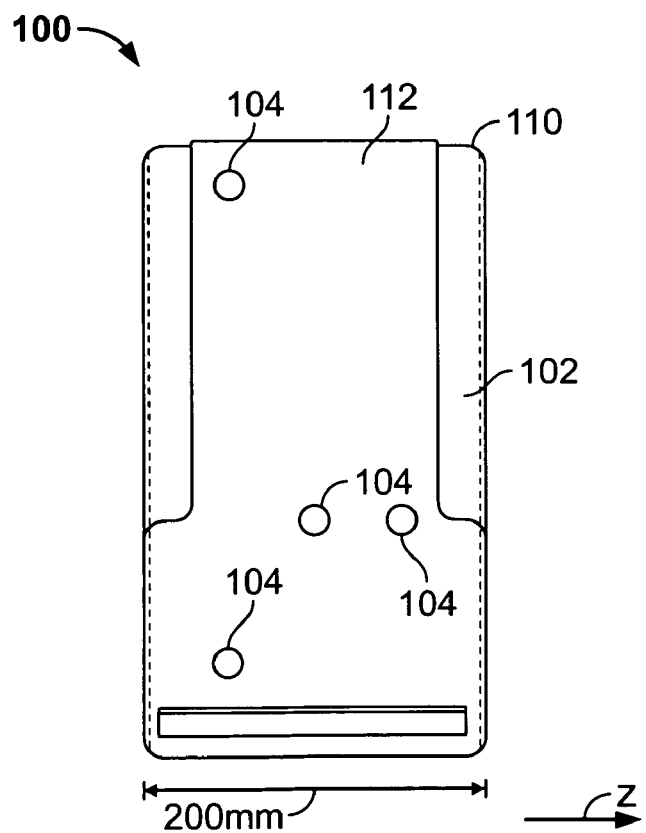
FIG. 4 is a side view of the exemplary alignment object shown in FIG. 3 in accordance with an embodiment of the present invention.

FIG. 3 is a front view of an exemplary alignment object 100 that may be used to align the multi-modal imaging system 10 in accordance with an embodiment of the present invention. FIG. 4 is a side view of the alignment object 100. The alignment object 100, or phantom 100, is used to both generate both attenuation data and emission data to facilitate aligning the multi-modal imaging system 10.

In the exemplary embodiment, the alignment object 100 includes a partially cylindrical body 102 and a plurality of target objects 104 embedded within the body 102. The body 102 has a curved lower surface that is substantially similar to the curvature of the imaging table 46. During operation, the curvature of the body's lower surface limits the movement of the alignment object 100 when placed on the imaging table 46. In the exemplary embodiment, the body 102 is fabricated from a material that does not produce significant attenuation, such as a foam polyurethane material, for example. Specifically, the body 102 may be fabricated from any material that has an attenuation coefficient that is less than the attenuation coefficient of the target objects 104. In the exemplary embodiment, the body 102 is fabricated using a material that has an attenuation coefficient that is an order of magnate less than the attenuation coefficient of the target objects 104. Optionally the body 102 may be fabricated from any material that holds the target objects 104 in a dimensionally stable position within the body 102 and does not affect the generation of either the attenuation data or emission data used to align the multi-modal imaging system 10. Although FIGS. 3 and 4 illustrate the alignment object 100 as having a spherical shape and a curved lower surface, it should be realized that this shape is exemplary only. The alignment object 100 may have any shape that facilitates aligning the multi-modal imaging system 10.

As shown in FIGS. 3 and 4, the alignment object 100 also includes the plurality of target objects 104 embedded in the body 102. In the exemplary embodiment, the alignment object 100 includes five spherical target objects 104 that are fabricated using a water-equivalent epoxy material, that is, a material that has a density approximately equivalent to the density of water, i.e. one gram per cc. For example, in one embodiment, each target object 104 is fabricated using a polyethylene material to form a shell 110 or outer surface of the target object 104. The shell 110 is then filled with a radioactive material or epoxy 112, to produce a radioactive target object 104.

Each of the target objects 104 has a diameter 120 that is predetermined based on the slice thicknesses produced by the multi-modal imaging system 10. For example, assuming that the CT imaging system generates multiple slices each having a thickness of approximately one millimeter, and the PET imaging system generates multiple slices each having a thickness of approximately 3.5 millimeters, the diameter 120 of the target objects 104 is greater than the slice thicknesses produced by either the CT imaging system or the PET imaging system. In the exemplary embodiment, the target objects 104 each have a diameter 120 that is approximately four to seven times larger than the slice thickness of either the PET slice. For example, assuming a known PET slice is approximately 3.5 millimeters thick, the diameter of the target objects 104 would each have a diameter that is between approximately fourteen millimeters and approximately 24.5 millimeters. In the exemplary embodiment the diameter 120 of each target object is approximately nineteen millimeters or approximately 5.5 times larger than the slice thickness of a PET image. Selecting the diameter 120 of the target objects larger than the slice thickness of the thickest slice produced by imaging system 10 ensures that each target object 104 will be visible in multiple CT slices and multiple PET slices to facilitate image registration as will be discussed below.

The target objects 104 are each located within the body 102 to enhance the imaging process. Specifically, each target object 104 is located over the field of view of the alignment object 100 along the X-axis, Y-axis, and Z-axis. For example, referring again to FIGS. 3 and 4, the target objects 104 are embedded within the alignment object 100 at specific locations to achieve a maximum error measurement between the transmission image data set and the emission image data set.

In the exemplary embodiment, the alignment object 100 includes five target objects 104. Optionally the alignment object 100 may include more than five target objects 104 to increase the accuracy of the data by providing duplicate target objects 104 within the alignment object 100. In another option, the alignment object 100 may include less than five target objects 104.

Figure 5A:
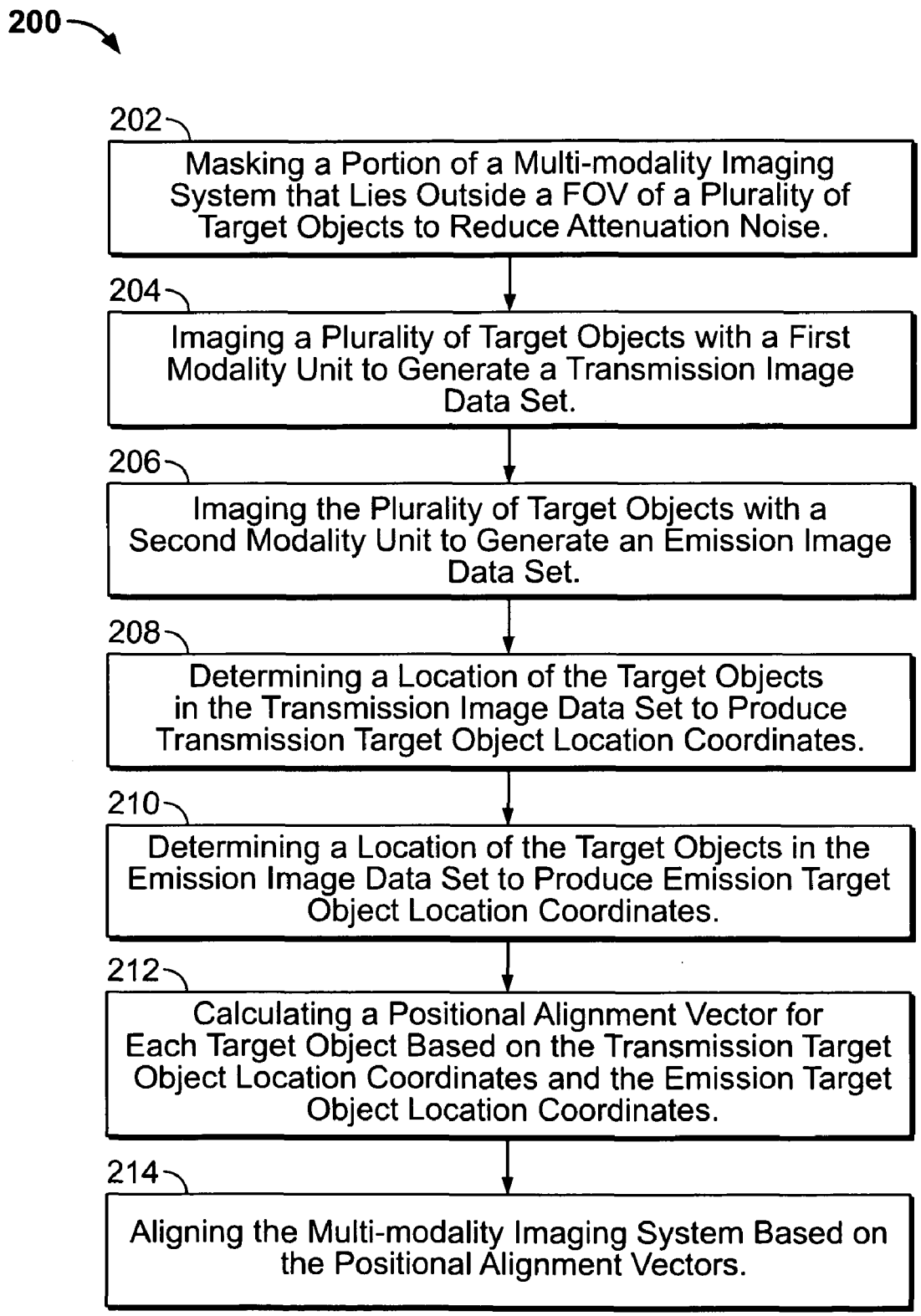
FIG. 5A is a flowchart of an exemplary method that for aligning the multi-modality imaging system shown in FIG. 1 in accordance with an embodiment of the present invention.
Figure 5B:
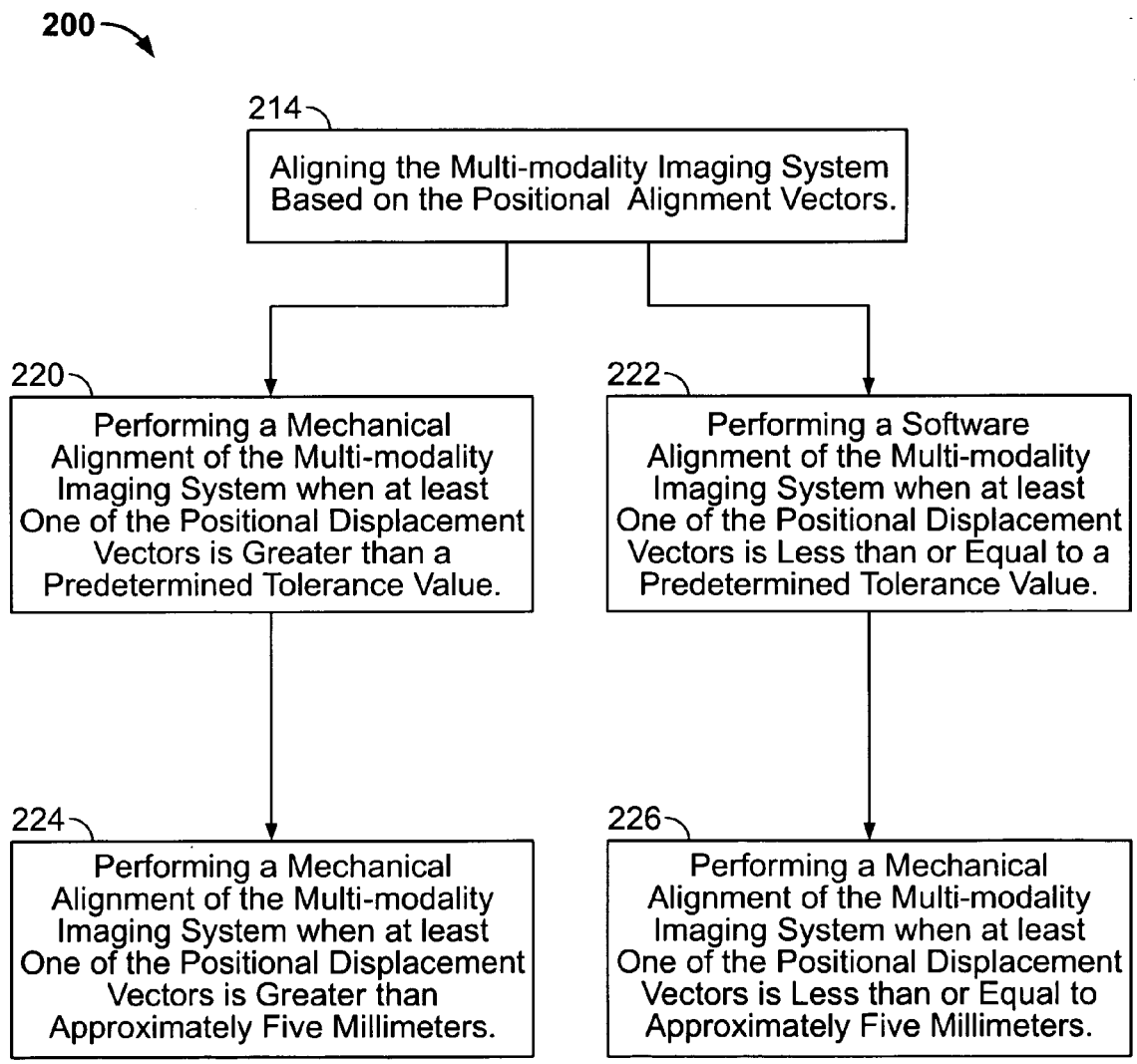
FIG. 5B is a flowchart illustrating a portion of the method shown in FIG. 5A in accordance with an embodiment of the present invention.

FIG. 5A is a flow chart illustrating an exemplary method 200 of determining component misalignment in a multi-modality imaging system including a first modality unit and a second modality unit, and a table. FIG. 5B is a flowchart illustrating detailed portion of the method 200 shown in FIG. 5A. As shown in FIG. 5A, the method 200 includes comprising masking 202 a portion of the multi-modality imaging system that lies outside of a field of view (FOV) of the plurality of target objects 104 to reduce attenuation noise. Method 200 also includes imaging 204 the plurality of target objects 104 with the first modality unit 11 to generate a transmission image data set and imaging 206 the plurality of target objects 104 with the second modality unit 12 to generate an emission image data set. A location of the target objects is then determined 208 in the transmission image data set and also determined 210 in the emission image data set to produce emission target object location coordinates. Method 200 also includes calculating 212 a positional alignment vector for each target object 104 based on the emission target object location coordinates, and aligning 214 the multi-modality imaging system 10 based on the positional alignment vectors.

Aligning 214 the multi-modality imaging system 10 based on the positional alignment vectors includes performing 220 a mechanical alignment of the multi-modality imaging system when at least one of the positional displacement vectors is greater than a predetermined tolerance value or performing 222 a software alignment of the multi-modality imaging system when at least one of the positional displacement vectors is less than or equal to the predetermined tolerance value. In the exemplary embodiment, the method 200 includes performing 224 a mechanical alignment of the multi-modality imaging system when at least one of the positional displacement vectors is greater than approximately five millimeters or performing 226 a software alignment of the multi-modality imaging system when at least one of the positional displacement vectors less than or equal to approximately five millimeters.

For example, in the exemplary embodiment, method 200 includes imaging 202 an object, such as alignment object 100, with the first modality unit 11 to generate an attenuation or transmission image data image set, and imaging 204 the alignment object 100 with the second modality unit 11 to generate an emission data image set. The method 200 also includes using 206 the transmission image data set and the emission data image set to align the multi-modality imaging system. As discussed above, in the exemplary embodiment, the first modality unit 11 is a CT imaging system and the second modality 12 is a PET imaging system. Optionally other imaging systems may be utilized to perform the method 200.

To perform method 200, the alignment object 100 is positioned within the multi-modality imaging system 10. The portion of the multi-modality imaging system 10 that lies generally outside the field of view (FOV) of the alignment object 100 is then masked 202 to reduce attenuation noise in the generated attenuation image set. For example, if the alignment object 100 is positioned on the imaging table 46, which may generate attenuation data that is observable in the transmission image data set, the portion of the imaging table 46 that lies outside the FOV of that alignment object 100 is masked to eliminate this attenuation data.

The alignment object 100 is then scanned using the CT imaging system 11 to generate the transmission image data set. The alignment object 100 is also scanned with the PET imaging system 12 to generate the emission data set. As discussed previously, the diameter 120 of the target objects 104 embedded within the alignment object or phantom 100 is sufficient such that the target objects are observed in a plurality of slices within each of the transmission image data set and the emission data image set.

A location of the target objects 104 in the transmission image data set is determined. A location of the five target objects 104 is also determined in the transmission image data set. In the exemplary embodiment, the alignment object 100 includes five target objects 104. The location or position of the five target objects 104 in the transmission image data set is determined 208 to generate transmission target object location coordinates. The location or position of the same five target objects 104 in the emission image data set is determined 210 to generate emission target object location coordinates. A single transmission target object coordinate represents a location of a single target in 3-D space in the transmission image data set. Moreover, a single emission target object coordinate represents a location of the same target in 3-D space in the emission image data set. In the exemplary embodiment, assuming five target objects 104 are imaged, method 200 includes determining a location of the five target objects in the transmission image data set and producing a single object location coordinate for each target object in the transmission image data set. Additionally method 200 includes determining a location of the five target objects in the emission image data set and producing a single object location coordinate for each target object in the emission image data set.

The transmission image data set is then registered with the emission data image set to generate a plurality of positional displacement vectors. The positional displacement vectors represent the spatial difference of the target objects 104 in three-dimensional space between the target object 104 located in the transmission image data set and the same target object 104 located in the emission data image. For example, calculating 212 a positional alignment vector for each target object 104 based on the transmission target object location coordinates and the emission data target object location coordinates. In the exemplary embodiment, the positional alignment vector is calculated by determining the spacial location difference by subtracting a transmission object location coordinates from the respective emission object locations coordinates, for example, to generate a single positional displacement vector for each target object 104 observed in both the transmission image data set and the emission image data set.

In the exemplary embodiment since the alignment object 100 includes five target objects 104, five positional displacement vectors, one for each target object 104 is calculated. The positional displacement vectors are then used to calculate a misalignment of the imaging table 46 relative to the PET imaging system 12 and/or to calculate a misalignment between the CT imaging system 11 and the PET imaging system 12.

In one embodiment, if at least one of the calculated positional displacement vectors is greater than a predetermined tolerance value, method 200 includes performing 220 a mechanical alignment. Optionally if at least one of the calculated positional displacement vectors is less than or equal to the predetermined tolerance value, method 200 includes performing 222 a software alignment. For example, if at least one of the positional displacement vectors is greater than approximately five millimeters, i.e. the displacement in three-dimensional space between a target object 104 located in the attenuation data set is greater than five millimeters from the same target object 104 located in the emission data image set, method 200 includes performing 226 a mechanical alignment. Optionally if at least one of the positional displacement vectors is less than approximately five millimeters, i.e. the displacement in three-dimensional space between a target object 104 located in the attenuation data set is less than or equal to five millimeters from the same target object 104 located in the emission data image set, method 200 includes performing 228 a software alignment. It should be realized that predetermined tolerance value is exemplary only and may be either increased or decreased based on the sensitivity of the imaging systems being aligned. For example, a software alignment may be performed when the predetermined tolerance value is equal to ten, i.e. the displacement in three-dimensional space between a target object 104 located in the attenuation data set is less than ten millimeters from the same target object 104 located in the emission data image set. The predetermined tolerance value may be selected between a range of approximately 3 millimeters and approximately 15 millimeters.

To perform 222 a software alignment, the positional displacement vectors are stored in the computer 36, for example, of the multi-modality imaging system 10. During typical patient scanning, if the patient is scanned with both the CT imaging system 11 and the PET imaging system 12, the computer 36 utilizes the positional displacement vectors to properly align the transmission image data set with the emission data image set during the registration process.

Optionally, if at least one of the calculated positional displacement vectors is greater than the predetermined tolerance value, a hardware alignment is performed. More specifically performing 220 a mechanical alignment further includes determining a table alignment status using the transmission image data set and the emission image data set by calculating at least one of a first modality unit to table alignment parameter and a second modality unit to table alignment parameter.

Figure 6:
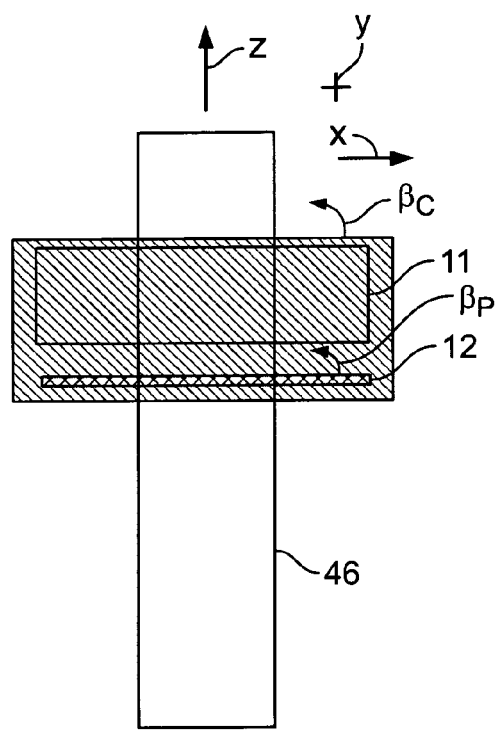
FIG. 6 is top view of the system shown in FIG. 1 in accordance with an embodiment of the present invention.
Figure 7:
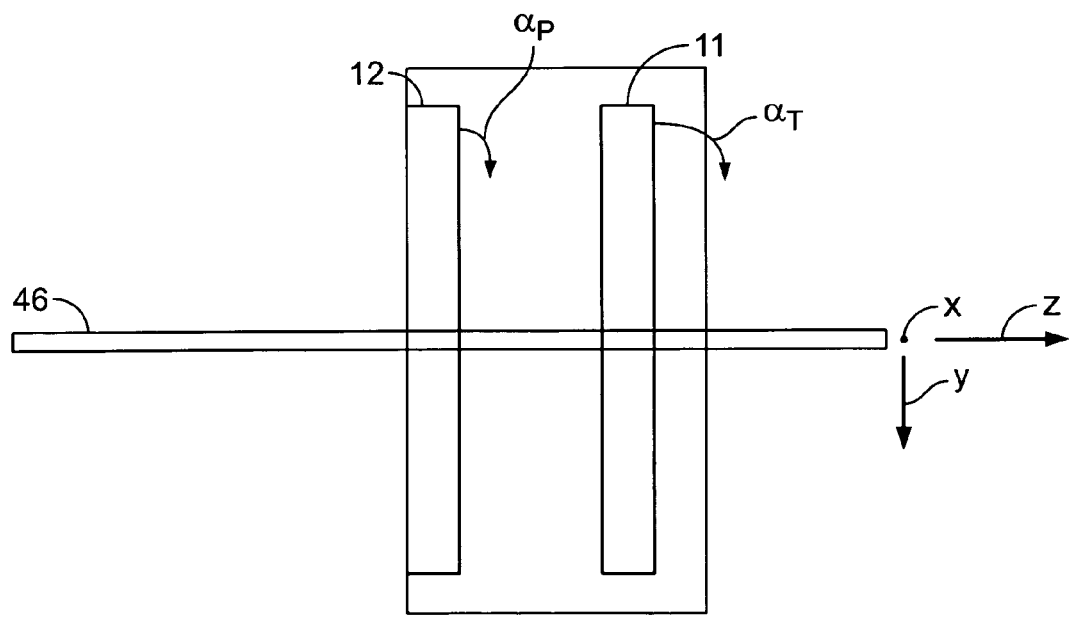
FIG. 7 is right view of the system shown in FIG. 1 in accordance with an embodiment of the present invention.
Figure 8:
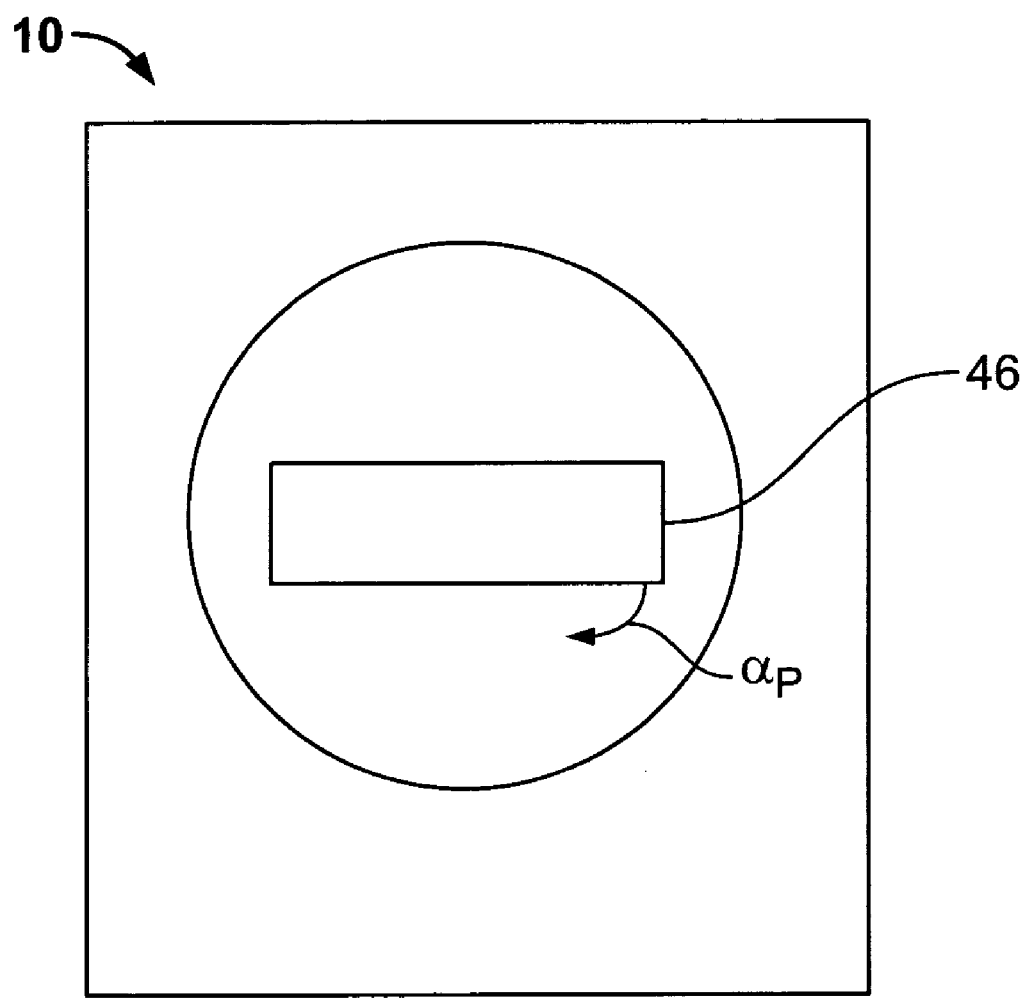
FIG. 8 is front view of the system shown in FIG. 1 in accordance with an embodiment of the present invention.

To perform 220 the mechanical alignment, the positional displacement vector for each target object 104, wherein each positional displacement vector is identified by a set of points, i.e. the transmission object location coordinates, identified in a single frame of the transmission image data set at coordinates $(x_{C1}, y_{C1}, z_{C1})$, i∈ [1, N] and the corresponding points $(x_{P1}, y_{P1}, z_{P1})$, i∈ [1, N] are identified in a singe-frame of the emission data image set and computes a set of alignment parameters. In the exemplary embodiment, a set of eight alignment parameters are computed. FIG. 6 is a top view, FIG. 7 is a right side view, and FIG. 8 is a front view of system 10 illustrating the eight parameters.

The alignment parameters include:

$P_x$ PET-to-table gantry linear misalignment in x (+x to right);
$P_y$ PET-to-table gantry linear misalignment in y (+y downward);
$P_z$ PET-to-table gantry linear misalignment in z (+z away from table);
$\alpha_P$ PET-to-table gantry tilt (+.alpha. top rotated forward);
$\beta_P$ P PET-to-table gantry yaw (+.beta. right side forward);
$\gamma_P$ PET-to-table (and CT) gantry roll (+.gamma. clockwise viewed from front);
$\beta_T$ Table-to-CT gantry yaw (+.beta. right side forward); and
$\alpha_T$ Table-to-CT gantry tilt (+.alpha. top rotated forward).

In operation, the algorithm has inputs that are matched CT-PET coordinate pairs (i.e., the positional displacement vectors). That is the points $(x_{C1}, y_{C1}, z_{C1})$ in CT image space are matched to the corresponding points of the positional vectors $(x_{P1}, y_{P1}, z_{P1})$ in PET image space). An output is the set of eight parameters discussed above.

In one embodiment the method includes computing sums of the following over all N point pairs: $x_P, y_P, z_P, x_P y_P, x_P z_P, y_P z_P, (x_P)^2, (y_P)^2, (z_P)^2, x_P y_c, x_P z_c, y_P z_c, x_c y_p, x_c z_p,$ and $y_c z_p$ and populating a transition matrix, T:

$$T \leftarrow \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix}$$

The transition matrix is used to calculate the parameters in accordance with $$\begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix} = \begin{pmatrix} N & 0 & 0 & 0 & -\sum z_P & -\sum y_P & 0 & 0 \\ 0 & N & 0 & \sum z_P & 0 & \sum x_P & 0 & 0 \\ 0 & 0 & N & -\sum y_P & \sum x_P & 0 & \sum x_P & -\sum y_P \\ 0 & \sum z_P & -\sum y_P & \sum y_P^2 + \sum z_P^2 & -\sum x_P y_P & \sum x_P z_P & -\sum x_P y_P & \sum y_P^2 \\ -\sum z_P & 0 & \sum x_P & -\sum x_P y_P & \sum x_P^2 + \sum z_P^2 & \sum y_P z_P & \sum x_P^2 & -\sum x_P y_P \\ -\sum y_P & \sum x_P & 0 & \sum x_P z_P & \sum y_P z_P & \sum x_P^2 + \sum y_P^2 & 0 & 0 \\ 0 & 0 & \sum x_P & -\sum x_P y_P & \sum x_P^2 & 0 & \sum x_P^2 & -\sum x_P y_P \\ 0 & 0 & -\sum y_P & \sum y_P^2 & -\sum x_P y_P & 0 & -\sum x_P y_P & \sum y_P^2 \end{pmatrix} \begin{pmatrix} P_x \\ P_y \\ P_z \\ \alpha_P \\ \beta_P \\ \gamma_P \\ \beta_T \\ \alpha_T \end{pmatrix}$$

Equation 1

In one embodiment, the method further includes computing the inverse of the T matrix, $T_1$. Optionally the inverse is not calculated, rather Equation (1) is solved directly by a means such as Gaussian elimination.

In one embodiment, using the inverse $T_1$, the method includes calculating the alignment parameters in accordance with:

$$\begin{pmatrix} P_x \\ P_y \\ P_z \\ \alpha_P \\ \beta_P \\ \gamma_P \\ \beta_T \\ \alpha_T \end{pmatrix} \leftarrow T^{-1} \cdot \begin{pmatrix} \sum x_C - x_P \\ \sum y_C - y_P \\ \sum z_C - z_P \\ \sum z_P y_C - y_P z_C \\ \sum x_P z_C - z_P x_C \\ \sum x_P y_C - y_P x_C \\ \sum x_P z_C - x_P z_P \\ \sum z_P y_P - y_P z_C \end{pmatrix}$$

Equation (2)

The above method was derived using small angle approximations such as x=sin x and 1=cos x, and, sometimes, the result is inaccurate because of the approximations. In cases where the above method yields an inaccurate result, the following two step method is useful to improve accuracy. The two step method includes using the above method to generate outputs $P_{x,0}$, $P_{y,0}$, $P_{z,0}$, $\alpha_{P,0}$, $\beta_{P,0}$, $\gamma_{P,0}$, $\beta_{T,0}$, and $\alpha_{T,0}$. Then an updated set of CT points ($x'_C$, $y'_C$, $z'_C$) are generated in accordance with:

$$\begin{pmatrix} x'_C \\ y'_C \\ z'_C \\ 1 \end{pmatrix} = \begin{pmatrix} \cos\beta_{T,0} & \sin\alpha_{T,0}\sin\beta_{T,0} & 0 & 0 \\ 0 & \cos\alpha_{T,0} & 0 & 0 \\ -\sin\beta_{T,0} & \sin\alpha_{T,0}\cos\beta_{T,0} & 1 & 0 \\ 0 & 0 & 0 & 1 \end{pmatrix} \begin{pmatrix} x_C \\ y_C \\ z_C \\ 1 \end{pmatrix}$$

An updated set of PET points is similarly generated according to:

$$\begin{pmatrix} x'_P \\ y'_P \\ z'_P \\ 1 \end{pmatrix} = \begin{pmatrix} 1 & 0 & 0 & 0 \\ 0 & \cos\alpha_{P,0} & \sin\alpha_{P,0} & 0 \\ 0 & -\sin\alpha_{P,0} & \cos\alpha_{P,0} & 0 \\ 0 & 0 & 0 & 1 \end{pmatrix} \begin{pmatrix} \cos\beta_{P,0} & 0 & -\sin\beta_{P,0} & 0 \\ 0 & 1 & 0 & 0 \\ \sin\beta_{P,0} & 0 & \cos\beta_{P,0} & 0 \\ 0 & 0 & 0 & 1 \end{pmatrix}$$

$$\begin{pmatrix} \cos\gamma_{P,0} & -\sin\gamma_{P,0} & 0 & 0 \\ \sin\gamma_{P,0} & \cos\gamma_{P,0} & 0 & 0 \\ 0 & 0 & 1 & 0 \\ 0 & 0 & 0 & 1 \end{pmatrix} \begin{pmatrix} 0 & 0 & 0 & P_{x,0} \\ 0 & 1 & 0 & P_{y,0} \\ 0 & 0 & 1 & P_{z,0} \\ 0 & 0 & 0 & 1 \end{pmatrix} \begin{pmatrix} x_P \\ y_P \\ z_P \\ 1 \end{pmatrix}$$

Using Equation 1 with ($x'_c$, $y'_c$, $z'_c$)–($x'_p$, $y'_p$, $z'_p$) as inputs, yields outputs of $P_{x,1}$, $P_{y,1}$, $P_{z,1}$, $\alpha_{P,1}$, $\beta_{P,1}$, $\gamma_{P,1}$, $\beta_{T,1}$, and $\alpha_{T,1}$. The final alignment parameters are then:

$$\begin{pmatrix} P_x \\ P_y \\ P_z \\ \alpha_P \\ \beta_P \\ \gamma_P \\ \beta_T \\ \alpha_T \end{pmatrix} = \begin{pmatrix} P_{x,0} \\ P_{y,0} \\ P_{z,0} \\ \alpha_{P,0} \\ \beta_{P,0} \\ \gamma_{P,0} \\ \beta_{T,0} \\ \alpha_{T,0} \end{pmatrix} + \begin{pmatrix} P_{x,1} \\ P_{y,1} \\ P_{z,1} \\ \alpha_{P,1} \\ \beta_{P,1} \\ \gamma_{P,1} \\ \beta_{T,1} \\ \alpha_{T,1} \end{pmatrix}$$

The parameters inform a user or an installer of system 10 as to a table alignment status (i.e., whether or not the table is misaligned with either the first modality unit 11 or the second modality unit 12, or more typically, both units because the units are substantially aligned to each other. Specifically both the $\alpha_T$ and $\beta_T$ parameters are utilized to align the imaging table 46, and the other six parameters are used to align the CT unit 11 with the PET unit 12. The installer can then re-align the table (adjust the axis of the table) with the gantry of the imaging system and repeat the herein described methods to verify if the re-aligned system is misaligned or not. Additionally as discussed above, the installer may perform a software alignment after the above described hardware alignment is completed. For example, the PET gantry roll can be corrected in the reconstruction software.

There is therefore provided efficient and cost effective methods and apparatus for determining component misalignment in multi-modal imaging systems. The herein described methods utilize both the CT attenuation data and the PET emission data to generate the positional displacement vectors. The positional displacement vectors are the utilized to calculate various table alignment parameters, such as the $\alpha_T$ and $\beta_T$ parameters while simultaneously determining gantry alignment through parameters $P_x$, $P_y$, $P_z$, $\alpha_P$, $\beta_P$, and $\gamma_P$.

Moreover, the above described methods and apparatus replace the known attenuation objects with alignment objects that are both attenuating and positron emitting. This allows the CT measurement to be done as attenuation and the PET measurement to be done with image reconstruction of emission. The alignment objects may be fabricated using water equivalent epoxy supported by a molded foam structure. Enhanced performance may be obtained with simple adjustment of the density thresholds. Further elaboration and performance improvement can be obtained with enhanced position determining algorithms that consider the effective centroid location and/or edge positions. Suitable performance is obtained in the PET imaging with a standard iterative reconstruction. Normalization, and activity calibration is therefore not required. The activity required in the emitting objects is minimal.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

As used herein, the term "computer" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory EEPROM memory and non-volatile RAM (NVRAM) memory. The above memory types are exemplary only and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method of determining component misalignment in a multi-modality imaging system including a first modality unit and a second modality unit, said method comprising:
   imaging a plurality of target objects with the second modality unit to generate an emission image data set;
   determining a location of the target objects in the emission image data set to produce emission target object location coordinates;
   calculating a positional alignment vector for each target object based on the emission target object location coordinates; and
   aligning the multi-modality imaging system based on the positional alignment vectors.

2. A method in accordance with claim 1 further comprising:
   imaging the plurality of target objects with the first modality unit to generate a transmission image data set;
   determining a location of the target objects in the transmission image data set to produce transmission target object location coordinates; and
   calculating a positional alignment vector for each target object based on the emission target object location coordinates and the transmission target object location coordinates.

3. A method in accordance with claim 1 further comprising masking a portion of the multi-modality imaging system mask that lies outside of a field of view of the plurality of target objects to reduce attenuation noise.

4. A method in accordance with claim 1 further comprising registering the emission image data set with a transmission image data set to calculate a positional alignment vector for each target object.

5. A method in accordance with claim 1 further comprising imaging an alignment object that includes the plurality of target objects embedded within the alignment object.

6. A method in accordance with claim 1 further comprising imaging an alignment object that includes the plurality of radioactive target objects embedded within an alignment object, wherein each of the target objects has a diameter that is greater than a slice thickness produced by either the first modality unit or the second modality unit.

7. A method in accordance with claim 1 further comprising imaging an alignment object that includes the plurality of radioactive target objects embedded within the alignment object, wherein each of the target objects has a diameter that is between three and six time larger than a thickness of an image slice produced by either the first modality unit or the second modality unit.

8. A method in accordance with claim 1 further comprising imaging an alignment object that includes the plurality of radioactive target objects embedded within the alignment object to achieve a maximum error measurement between the emission image data set and a transmission image data set.

9. A method in accordance with claim 1 wherein the second modality comprises a PET imaging system said method further comprising calculating a misalignment of an imaging table relative to the PET imaging system based on the positional displacement vectors.

10. A method in accordance with claim 1 wherein the first modality comprises a CT imaging system and the second modality comprises a PET imaging system said method further comprising calculating a misalignment of the CT imaging system relative to the PET imaging system based on the positional displacement vectors.

11. A method in accordance with claim 1 further comprising performing a mechanical alignment of the multi-modality imaging system when at least one of the positional displacement vectors is greater than a predetermined tolerance value.

12. A method in accordance with claim 1 further comprising performing a mechanical alignment of the multi-modality imaging system when at least one of the positional displacement vectors is greater than approximately five millimeters.

13. A method in accordance with claim 1 further comprising performing a software alignment of the multi-modality imaging system when at least one of the positional displacement vectors is less than or equal to a predetermined tolerance value.

14. A method in accordance with claim 1 further comprising performing a software alignment of the multi-modality imaging system when at least one of the positional displacement vectors is less than approximately five millimeters.

15. A method in accordance with claim 1 wherein the first modality comprises a CT imaging system and the second modality comprises a PET imaging system said method further comprising calculating at least one of a PET unit to table gantry linear misalignment in x parameter, a PET unit to table gantry linear misalignment in y parameter, a PET unit to table gantry linear misalignment in z parameter, a PET unit to table gantry tilt parameter, a PET unit to table gantry vase parameter, a gantry roll parameter, a CT unit to table gantry tilt parameter, and a PET unit to gantry yaw parameter.

16. A multi-modality imaging system comprising a first modality unit, a second modality unit, and a computer operationally coupled to the first and second modality units, wherein the computer is programmed to:
   image a plurality of target objects with the second modality unit to generate an emission image data set;
   determine a location of the target objects in the emission image data set to produce emission target object location coordinates; and
   calculate a positional alignment vector for each target object based on the emission target object location coordinates, the positional alignment vectors used to align the multi-modality imaging system.

17. A multi-modality imaging system in accordance with claim 16, wherein the computer is further programmed to:
   image a plurality of target objects with the first modality unit to generate a transmission image data set;
   determine a location of the target objects in the transmission image data set to produce transmission target object location coordinates; and calculate the positional alignment vector for each target object based on the target transmission target object location coordinates.

18. A multi-modality imaging system in accordance with claim 16, wherein the computer is further programmed to generate an indication to perform a mechanical alignment if at least one of the positional displacement vectors is greater than a predetermined tolerance value.

19. A multi-modality imaging system in accordance with claim 16, wherein the computer is further programmed to generate an indication to perform a software alignment if at least one of the positional displacement vectors is less than or equal to a predetermined tolerance value.

20. A multi-modality imaging system in accordance with claim 16, wherein the computer is further programmed to calculate a matrix T that includes a number of points in a first modality image space that match points in a second modality imaging space.

21. A multi-modality imaging system in accordance with claim 16, wherein the computer is further programmed to calculate the inverse (I) to the matrix.

22. A computer readable medium encoded with a program programmed to instruct a computer to:
  image a plurality of target objects with the second modality unit to generate an emission image data set;
  determine a location of the target objects in the emission image data set to produce emission target object location coordinates; and
  calculate a positional alignment vector for each target object based on the emission target object location coordinates, the positional alignment vectors used to align the multi-modality imaging system.

23. A computer readable medium in accordance with claim 22 wherein the computer readable medium is further programmed to:
  image a plurality of target objects with the first modality unit to generate a transmission image data set;
  determine a location of the target objects in the transmission image data set to produce transmission target object location coordinates; and
  calculate the positional alignment vector for each target object based on the target transmission target object location coordinates.

24. A computer readable medium in accordance with claim 22 wherein the computer readable medium is further programmed to use the positional displacement vectors to calculate a misalignment of the table relative to the second modality unit and to calculate a misalignment between the first modality unit and the second modality unit.

25. A computer readable medium in accordance with claim 22 wherein the computer readable medium is further programmed to calculate a matrix T that includes a number of points in a first modality image space that match points in a second modality imaging space.

26. A computer readable medium in accordance with claim 24 wherein the computer readable medium is further programmed to calculate the inverse (I) to the matrix T.

\* \* \* \* \*

UNITED STATES PATENT AND TRADEMARK OFFICE
CERTIFICATE OF CORRECTION

| | | |
|---|---|---|
| PATENT NO. | : 8,077,943 B2 | Page 1 of 1 |
| APPLICATION NO. | : 12/045246 | |
| DATED | : December 13, 2011 | |
| INVENTOR(S) | : Williams et al. | |

It is certified that error appears in the above-identified patent and that said Letters Patent is hereby corrected as shown below:

IN THE CLAIMS:

In Column 16, Line 45, in Claim 15, delete "vase" and insert -- yaw --, therefor.

Signed and Sealed this
Third Day of April, 2012

David J. Kappos
*Director of the United States Patent and Trademark Office*